US010682506B2

(12) United States Patent
Iwakata et al.

(10) Patent No.: US 10,682,506 B2
(45) Date of Patent: Jun. 16, 2020

(54) CONNECTING STRUCTURE FOR MEDICAL USE

(71) Applicant: KOYO SANGYO CO., LTD., Tokyo (JP)

(72) Inventors: Mario Iwakata, Joetsu (JP); Hiroki Watanabe, Joetsu (JP); Takayuki Miyazaki, Joetsu (JP)

(73) Assignee: Koyo Sangyo Co., Ltd., Tokyo (JP)

( * ) Notice: Subject to any disclaimer, the term of this patent is extended or adjusted under 35 U.S.C. 154(b) by 217 days.

(21) Appl. No.: 15/571,419

(22) PCT Filed: Apr. 12, 2017

(86) PCT No.: PCT/JP2017/015018
§ 371 (c)(1),
(2) Date: Nov. 2, 2017

(87) PCT Pub. No.: WO2018/189842
PCT Pub. Date: Oct. 18, 2018

(65) Prior Publication Data
US 2018/0369559 A1  Dec. 27, 2018

(51) Int. Cl.
*A61M 39/10* (2006.01)
*A61M 39/22* (2006.01)

(52) U.S. Cl.
CPC ........ *A61M 39/1011* (2013.01); *A61M 39/10* (2013.01); *A61M 39/22* (2013.01);
(Continued)

(58) Field of Classification Search
CPC ...... A61M 39/1011; A61M 2039/1033; A61M 2039/1038; A61M 2039/1066
See application file for complete search history.

(56) References Cited

U.S. PATENT DOCUMENTS

2008/0287920 A1* 11/2008 Fangrow ............ A61M 39/1011
604/535
2015/0051555 A1  2/2015 Fangrow, Jr. et al.

FOREIGN PATENT DOCUMENTS

EP  2030647 A1  3/2009
EP  3108926 A1  12/2016
(Continued)

OTHER PUBLICATIONS

English translation of Written Opinion of the International Searching Authority for PCT/JP2017/015018 dated Feb. 5, 2018.
(Continued)

*Primary Examiner* — Nathan R Price
*Assistant Examiner* — Melissa A Snyder
(74) *Attorney, Agent, or Firm* — Thomas B. Ryan; Jodi A. Reynolds, Esq.; Harter Secrest & Emery LLP

(57) ABSTRACT

A connecting structure for medical use includes a male assembly (1) and a female connector (2) having a cylindrical configuration. The male assembly (1) includes a male connector (10) having a cylindrical configuration and a threadedly engageable cylinder (20) rotatably coupled to the male connector (10). A male luer portion (11) of the male connector (10) and a female luer portion (2a) of the female connector (2) are joined by turning the threadedly engageable cylinder (20) in a tightening direction when a female screw (21a) of the threadedly engageable cylinder (20) and an engageable protrusion (2c) of the female connector (2) are threadedly engaged with each other. The connecting structure for medical use further includes a loosening prevention mechanism (30) that prohibits rotation of the threadedly engageable cylinder (20) in a loosening direction with respect to the male connector (10) when the male luer portion (11) and the female luer portion (2a) are joined. The loosening prevention mechanism (30) includes ratchet teeth (31) formed in an inner periphery of the threadedly engage-
(Continued)

able cylinder (20), an elastic projection (32) formed in the male connector (10) and an engageable claw (33) protruded from a free end of the elastic projection (32) and engageable with the ratchet teeth.

10 Claims, 14 Drawing Sheets

(52) U.S. Cl.
CPC ............... *A61M 2039/1033* (2013.01); *A61M 2039/1038* (2013.01); *A61M 2039/1066* (2013.01); *A61M 2039/229* (2013.01); *A61M 2205/0216* (2013.01)

(56) References Cited

FOREIGN PATENT DOCUMENTS

| | | |
|---|---|---|
| JP | S59-087840 U | 6/1984 |
| JP | 2010-527276 A | 8/2010 |
| WO | 2016/157974 A1 | 10/2016 |
| WO | 2017008012 A1 | 1/2017 |

OTHER PUBLICATIONS

International Search Report for PCT/JP2017/015018 dated Jul. 18, 2017.
Extended European Search Report dated Nov. 23, 2018 on European Patent Application No. EP17801319.9.
International Preliminary Report on Patentability from International Application No. PCT/JP2017/015018, dated Oct. 15, 2019.

\* cited by examiner

CONNECTING STRUCTURE FOR MEDICAL USE

FIELD OF THE INVENTION

The present invention relates to a connecting structure for medical use.

BACKGROUND OF THE INVENTION

There are various types of connecting structures for medical use for connecting medical components such as tubes. A connecting structure for medical use of the type disclosed in Patent Document 1 (Unexamined Utility Model Publication No. S59-87840) is described below with reference to FIGS. 22 and 23.

The connecting structure for medical use includes a male assembly 1 and a female connector 2.

The male assembly 1 includes a male connector 10 and a threadedly engageable cylinder 20 rotatably attached to the male connector 10. The male connector 10 includes a male luer portion 11 having a tapered outer periphery. The threadedly engageable cylinder 20 includes a threadedly engageable portion 21 disposed outside of the male luer portion 11 of the male connector 10 in a radial direction. A female screw 21a is formed in an inner periphery of the threadedly engageable portion 21.

The female connector 2 includes a female luer portion 2a having a tapered inner periphery. Engageable protrusions 2c threadedly engageable with the female screw 21a is formed in an outer periphery of a distal end portion of the female luer portion 2a.

As shown in FIG. 22, when the threadedly engageable cylinder 20 is turned in a tightening direction with the female screw 21a of the threadedly engageable cylinder 20 and the engageable protrusions 2c of the female connector 2 threadedly engaged, the male luer portion 11 and the female luer portion 2a are joined together. When the threadedly engageable cylinder 20 is turned further in the tightening direction, the male luer portion 11 and the female luer portion 2a are tightly joined together with a pressing force, providing sufficient sealing properties.

When the threadedly engageable cylinder 20 is in a tightened state, a surface 21x on a deeper side of a screw thread of the female screw 21a is strongly abutted against the engageable protrusions 2c, thereby drawing the female luer portion 2a toward the male luer portion 11. By friction between the surface 21x on the deeper side of the screw thread of the female screw 21a and the engageable protrusions 2c, the threadedly engageable cylinder 20 keeps the female luer portion 2a in the drawn state, thereby keeping the male luer portion 11 and the female luer portion 2a in the joined state.

SUMMARY OF THE INVENTION

Problem to be Solved by the Invention

However, as shown in FIG. 22, there is a gap G in an axial direction between a surface 21y on an open end side of the screw thread of the female screw 21a and the engageable protrusions 2c, and by a vibration or unintentional application of torque, the threadedly engageable cylinder 20 may be rotated through an angle corresponding to the gap G in a loosening direction as shown in FIG. 23. This causes the surface 21y on the open end side of the screw thread of the female screw 21a to be abutted against the engageable protrusions 2c, thereby forming a gap G between the surface 21x on the deeper side of the screw thread and the engageable protrusions 2c. When fluid flows in the connecting structure in this condition, pressure of the fluid causes the male luer portion 11 and the female luer portion 2a to be displaced in a separating direction through a distance corresponding to the gap G. As a result, sufficient sealing properties may not be achieved, causing the fluid to leak from between the male luer portion 11 and the female luer portion 2a.

The connecting structure for medical use disclosed in FIGS. 1 to 6 of the Patent Document 2 (WO2016/157974) is provided with a torque limiting mechanism developed by the inventors of the present application. As with the one shown in FIGS. 22 and 23 of Patent Document 1, the threadedly engageable cylinder is not prohibited from being rotated in the loosening direction in the connecting structure for medical use disclosed in Patent Document 2.

Means for Solving the Problems

To solve the problems mentioned above, the present invention provides a connecting structure for medical use including: a male assembly; and a female connector having a cylindrical configuration, the male assembly including a male connector having a cylindrical configuration and a threadedly engageable cylinder rotatably coupled to the male connector, the male connector including a male luer portion and a support portion arranged in a direction from a distal end to a basal end of the male connector in this order, the threadedly engageable cylinder including a threadedly engageable portion and a mounting portion arranged in a direction from a distal end to a basal end of the threadedly engageable cylinder in this order, the mounting portion rotatably mounted to an outer periphery of the support portion of the male connector, the threadedly engageable portion having a female screw in an inner periphery thereof, the threadedly engageable portion disposed outside of the male luer portion in a radial direction, the female connector including a female luer portion and an engageable protrusion formed in an outer periphery of the female luer portion, the male luer portion and the female luer portion joined by turning the threadedly engageable cylinder in a tightening direction in a state where the female screw of the threadedly engageable cylinder is threadedly engaged with the engageable protrusion of the female connector, wherein a loosening prevention mechanism is disposed between the support portion of the male connector and the mounting portion of the threadedly engageable cylinder, the loosening prevention mechanism prohibiting the threadedly engageable cylinder from being rotated in a loosening direction with respect to the male connector in a state where the male luer portion and the female luer portion are joined.

According to the features mentioned above, in a state where the male luer portion and the female luer portion are joined, the threadedly engageable cylinder is prohibited from being rotated in the loosening direction with respect to the male connector. Therefore, sealing properties between the male luer portion and the female luer portion can be maintained, thereby surely preventing leakage of fluid.

Preferably, the loosening prevention mechanism includes: ratchet teeth formed in one of the support portion of the male connector and the mounting portion of the threadedly engageable cylinder over an entire periphery; at least one elastic projection formed in the other of the support portion and the mounting portion; and an engageable claw formed in a free end of the elastic projection and engageable with the ratchet teeth.

Preferably, an annular gap is formed between the support portion of the male connector and the mounting portion of the threadedly engageable cylinder; the ratchet teeth facing the annular gap are formed in an inner periphery of the mounting portion of the threadedly engageable cylinder; the elastic projection is formed in the support portion of the male connector and disposed in the annular gap; and the engageable claw is protruded outwardly in a radial direction from the free end of the elastic projection and engaged with the ratchet teeth.

According to the features mentioned above, since the loosening prevention mechanism is covered by the threadedly engageable cylinder, the loosening prevention mechanism is protected from dust.

Preferably, the support portion of the male connector includes a support surface facing the annular gap and extending in the radial direction; and the elastic projection extends in an axial direction of the male connector from the support surface.

Preferably, the ratchet teeth are formed in an outer periphery of the support portion of the male connector; the elastic projection is formed in the mounting portion of the threadedly engageable cylinder; and the engageable claw is protruded inwardly in a radial direction and engaged with the ratchet teeth.

More preferably, a slit having a L-shaped configuration is formed in an end portion of the mounting portion of the threadedly engageable cylinder; and the elastic projection extending in a circumferential direction is defined by the slit.

Preferably, the connecting structure for medical use further includes: an operation cylinder mounted on an outer periphery of the threadedly engageable cylinder; and a torque limiting mechanism disposed between the threadedly engageable cylinder and the operation cylinder, wherein: the torque limiting mechanism transmits a rotary torque in a tightening direction of the operation cylinder to the threadedly engageable cylinder; and the torque limiting mechanism allows the operation cylinder to turn idly with respect to the threadedly engageable cylinder when the rotary torque exceeds a predetermined torque.

According to the features mentioned above, excessive tightening by the threadedly engageable cylinder can be prohibited, and thereby joining of the male luer portion and the female luer portion by excessive force can be prohibited.

Preferably, the connecting structure for medical use further includes: an operation cylinder mounted on an outer periphery of the threadedly engageable cylinder; and a torque limiting mechanism disposed between the threadedly engageable cylinder and the operation cylinder, wherein: the torque limiting mechanism transmits a rotary torque in a tightening direction of the operation cylinder to the threadedly engageable cylinder; the torque limiting mechanism allows the operation cylinder to turn idly with respect to the threadedly engageable cylinder when the rotary torque exceeds a predetermined torque; the torque limiting mechanism includes engageable teeth formed in one of the threadedly engageable cylinder and the operation cylinder over an entire periphery, at least one second elastic projection formed in the other of the threadedly engageable cylinder and the operation cylinder and second engageable claw formed in the second elastic projection and engaged with the engageable teeth; and an elastic coefficient of the second elastic projection is greater than an elastic coefficient of the elastic projection of the loosening prevention mechanism.

Preferably, the engageable teeth are formed in an inner periphery of the operation cylinder; the second elastic projection is formed in the threadedly engageable cylinder; and the second engageable claw is protruded outwardly in a radial direction and engaged with the engageable teeth.

According to the features mentioned above, the torque limiting mechanism can be covered with the operation cylinder, and thereby the torque limiting mechanism can be protected from dust.

In one aspect of the present invention, a slit having a L-shaped configuration is formed in an end portion of the mounting portion of the threadedly engageable cylinder; the second elastic projection of the torque limiting mechanism is defined by the slit; the ratchet teeth of the loosening prevention mechanism are formed in an inner periphery of the mounting portion of the threadedly engageable cylinder and disposed adjacent to the second elastic projection in an axial direction; the elastic projection of the loosening prevention mechanism is formed in the support portion of the male connector; and the engageable claw is protruded outwardly in a radial direction from the free end of the elastic projection and engaged with the ratchet teeth.

In another aspect of the present invention, an annular gap is formed between the threadedly engageable cylinder and the operation cylinder; the ratchet teeth facing the annular gap are formed in the inner periphery of the operation cylinder; the threadedly engageable cylinder includes a support surface facing the annular gap and extending in the radial direction; and the second elastic projection extending in an axial direction of the threadedly engageable cylinder from the support surface is disposed in the annular gap.

Advantageous Effects of the Invention

According to the present invention, appropriate sealing properties can be surely maintained in a connecting structure for medical use.

MODE FOR CARRYING OUT THE INVENTION

Figure 1:
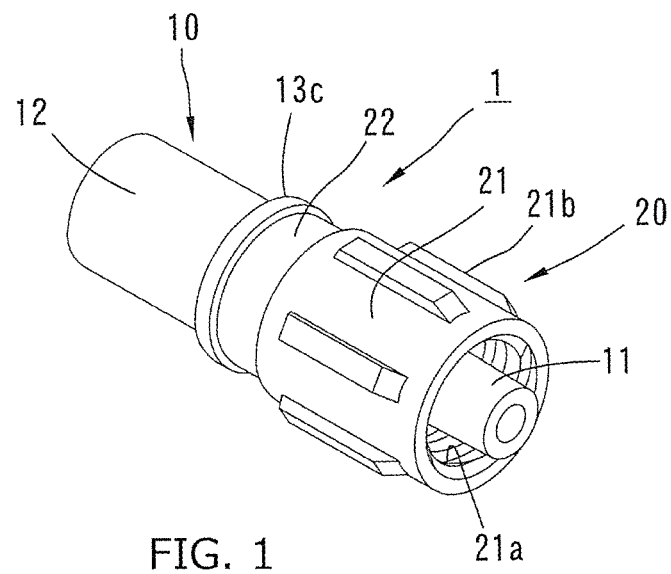
FIG. 1 is a perspective view of a male assembly of a connecting structure for medical use according to a first embodiment of the present invention.
Figure 2:
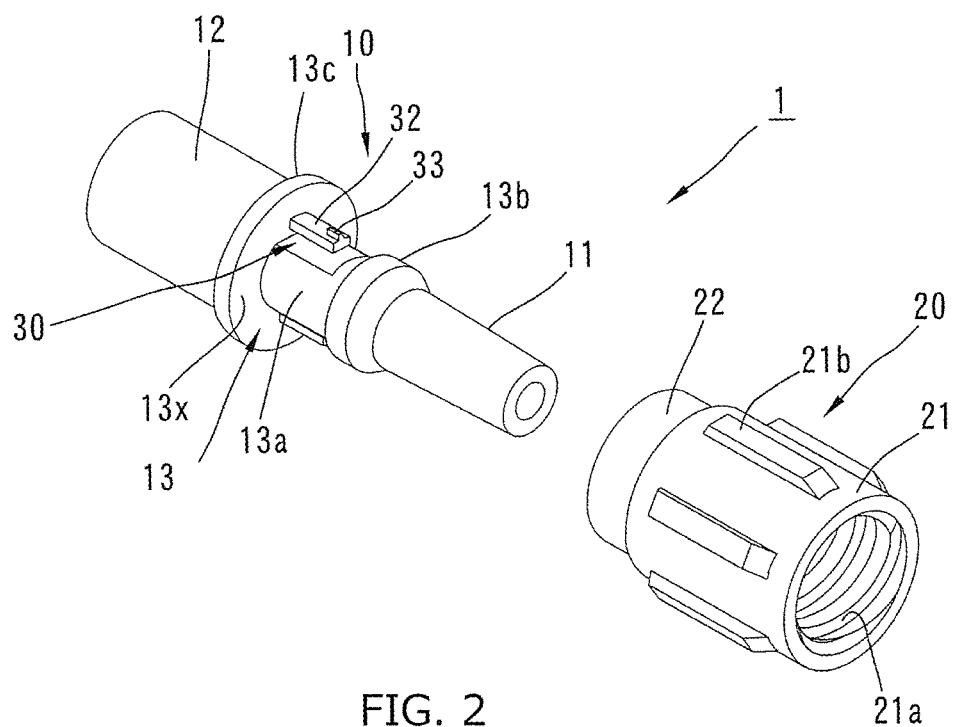
FIG. 2 is an exploded perspective view of the male assembly.
Figure 3:
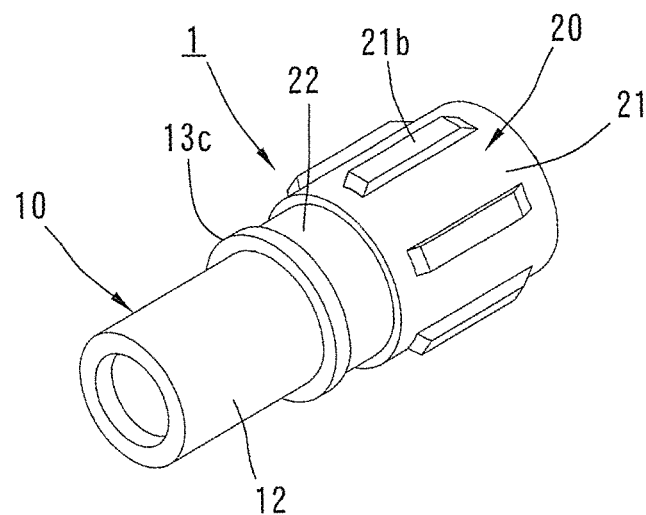
FIG. 3 is a perspective view of the male assembly, viewed from a different direction from that of FIG. 1.
Figure 4:
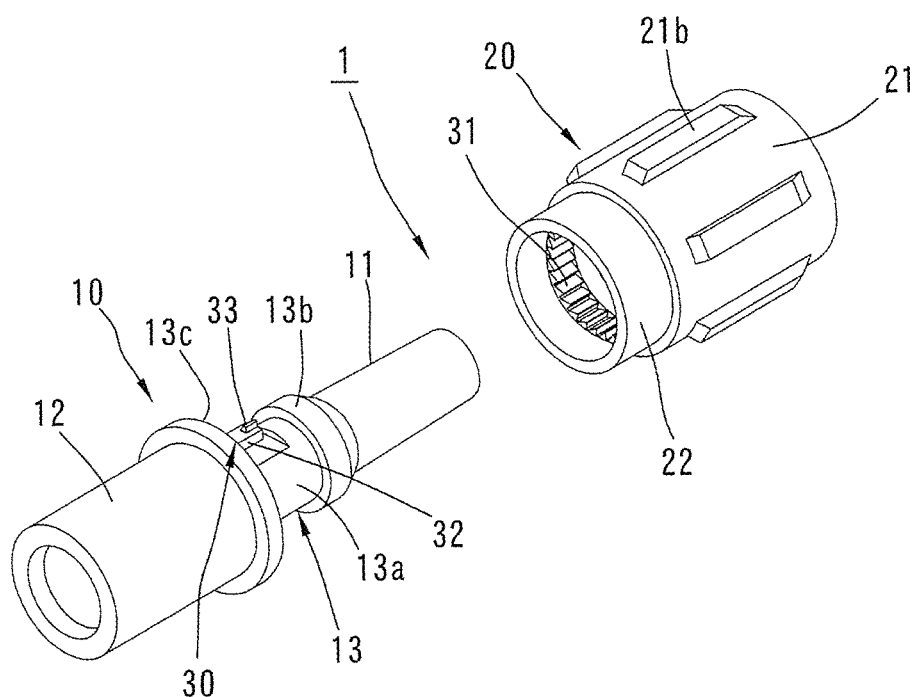
FIG. 4 is an exploded perspective view of the male assembly, viewed from a different direction from that of FIG. 2.

Details of the present invention will be described hereinafter with reference to the drawings.

FIGS. 1 to 6 show a connecting structure for medical use according to a first embodiment of the present invention, which is applied to connect tubes 5, 5' (first and second medical components, shown only in FIG. 5) in which liquid such as medical solution and blood is to be flown. The connecting structure includes a male assembly 1 made of resin and a female connector 2 (shown only in FIG. 5) made of resin.

The female connector 2 having a simpler structure will be described first with reference to FIG. 5. The female connector 2 having a thin and long cylindrical configuration includes a female luer portion 2a in one end portion (distal end portion) thereof in an axial direction and a coupling portion 2b in the other end portion (basal end portion) thereof. An inner periphery of the female luer portion 2a has a gently tapered configuration whose diameter is gradually increased towards a distal end of the female luer portion 2a.

A pair of engageable protrusions 2c that work as male screws are formed in an outer periphery of a distal end portion of the female luer portion 2a 180 degrees apart from each other in a circumferential direction. Elongated raised portions 2d for placing fingers thereon are formed in an intermediate portion of the female connector 2 in the axial direction. An end portion of the tube 5' is to be inserted into and fixed at the coupling portion 2b.

As shown in FIGS. 1 to 4, the male assembly 1 includes a male connector 10 and a threadedly engageable cylinder 20 mounted on an outer periphery of the male connector 10 such that the threadedly engageable cylinder 20 is rotatable but immovable in an axial direction.

The male connector 10 has a thin and long cylindrical configuration. The male connector 10 includes a male luer portion 11 in one end portion (distal end portion) thereof in an axial direction and a coupling portion 12 in the other end portion (basal end portion) thereof. An outer periphery of the male luer portion 11 has a gently tapered configuration whose diameter is gradually reduced towards a distal end of the male luer portion 11. A taper angle of the outer periphery of the male luer portion 11 and a taper angle of the inner periphery of the female luer portion 2a are substantially the same. An end portion of the tube 5 is to be inserted into and fixed at the coupling portion 12.

An intermediate portion of the male connector 10 in the axial direction is provided as a support portion 13 for rotatably supporting the threadedly engageable cylinder 20. The support portion 13 includes a small-diameter cylindrical portion 13a, an annular protrusion 13b and a flange portion 13c. The annular protrusion 13b is formed in an outer periphery of a boundary portion between the small-diameter cylindrical portion 13a and the male luer portion 11. The flange portion 13c is formed in an outer periphery of a boundary portion between the small-diameter cylindrical portion 13a and the coupling portion 12.

The threadedly engageable cylinder 20 includes a threadedly engageable portion 21 in one end portion (distal end portion) thereof in the axial direction and a mounting portion 22 in the other end portion (basal end portion) thereof. A female screw 21a is formed in an inner periphery of the threadedly engageable portion 21. Elongated raised portions 21b for placing fingers thereon are formed in an outer periphery of the threadedly engageable portion 21.

Figure 5:
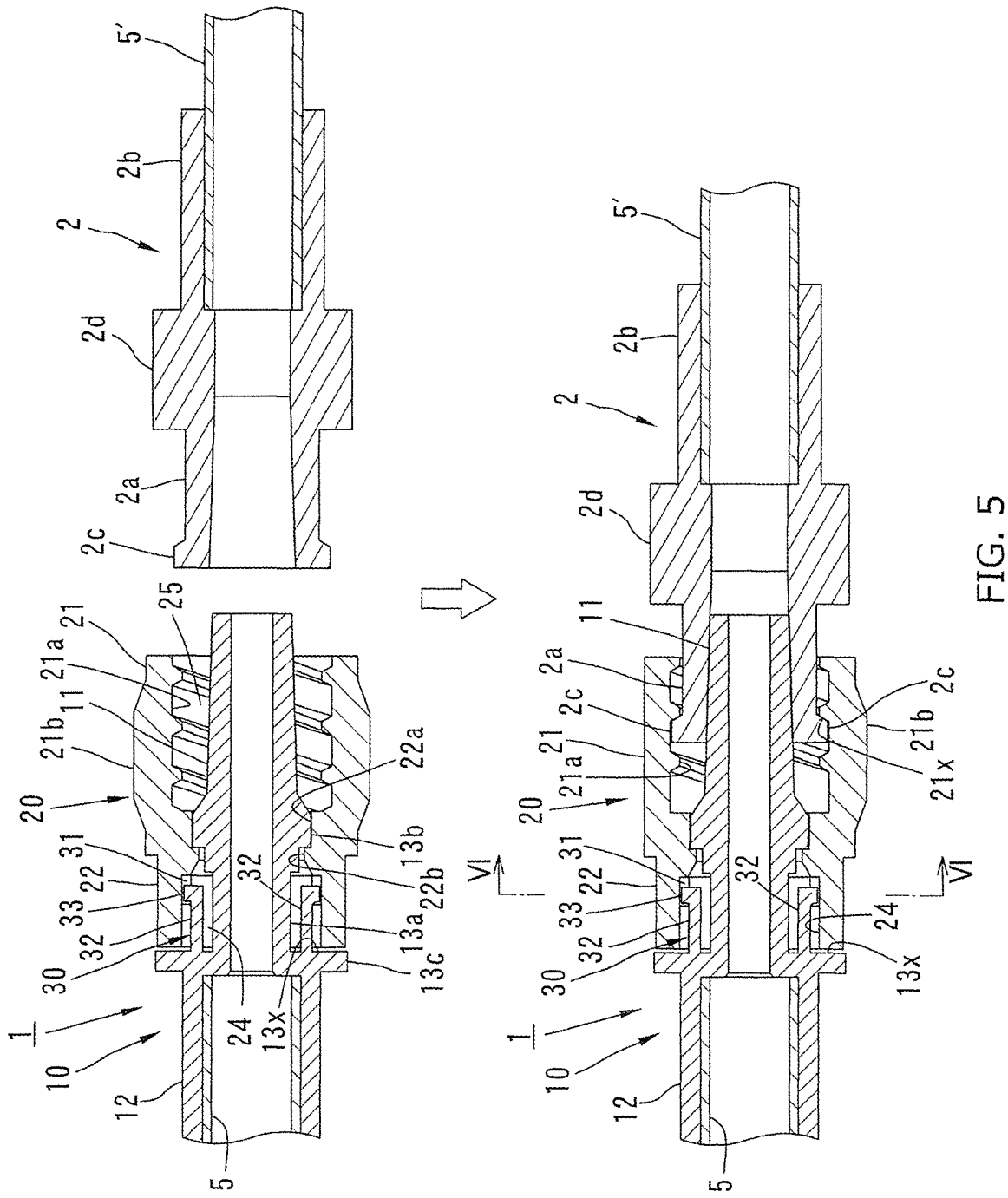
FIG. 5 is a longitudinal sectional view of the connecting structure for medical use applied to connect tubes, showing the male assembly and a female connector before being connected above the arrow and showing the male assembly and the female connector after being connected below the arrow.

As shown in FIG. 5, an annular abutment surface 22a is formed in an inner periphery of the mounting portion 22 of the threadedly engageable cylinder 20 adjacent to the female screw 21a. An annular catch protrusion 22b is formed next to the abutment surface 22a.

The abutment surface 22a of the threadedly engageable cylinder 20 is abutted against an outer periphery of the annular protrusion 13b of the male connector 10 and the catch protrusion 22b is caught by the annular protrusion 13b and a basal end of the mounting portion 22 is caught by the flange portion 13c of the male connector 10. Thereby, the threadedly engageable cylinder 20 is mounted on the male connector 10 such that the threadedly engageable cylinder 20 is rotatable but relatively immovable in the axial direction with respect to the male connector 10.

In a state where the threadedly engageable cylinder 20 is mounted on the male connector 10, an annular gap 24 is formed between the small-diameter cylindrical portion 13a of the male connector 10 and the mounting portion 22 of the threadedly engageable cylinder 20.

In the state where the threadedly engageable cylinder 20 is mounted on the male connector 10, an annular insertion space 25 is formed between the threadedly engageable portion 21 of the threadedly engageable cylinder 20 and the male luer portion 11 of the male connector 10. The female screw 21a is disposed outside of the male luer portion 11 in a radial direction.

The male assembly 1 includes a loosening prevention mechanism 30 disposed between the male connector 10 and the threadedly engageable cylinder 20. The loosening prevention mechanism 30 has ratchet teeth 31 formed all around the inner periphery of the mounting portion 22 of the threadedly engageable cylinder 20 and a pair of elastic projections 32 formed in the flange portion 13c of the male connector 10. More specifically, the flange portion 13c includes an annular support surface 13x facing the annular gap 24 and extending in the radial direction. The elastic projections 32 extend in the axial direction from the support surface 13x toward the male luer portion 11.

Figure 6A:
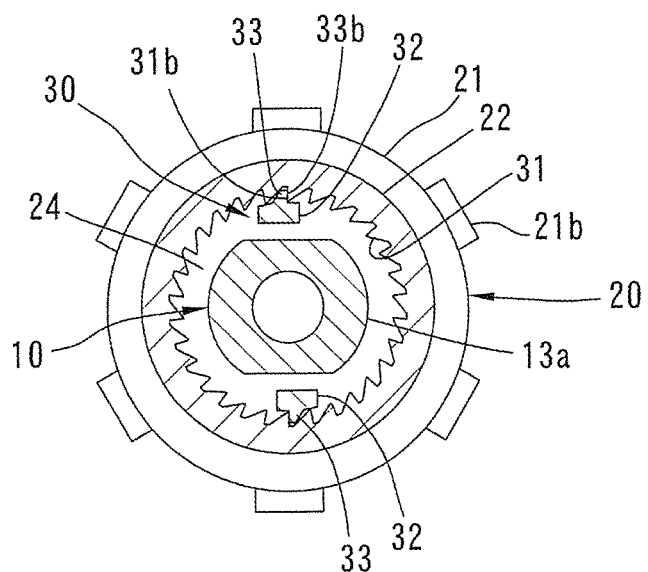
FIG. 6A is a cross-sectional view taken along line VI-VI of FIG. 5, showing engageable claws of a male connector and ratchet teeth of a threadedly engageable cylinder constituting a loosening prevention mechanism engaged with one another.

As shown in FIGS. 5 and 6A, the pair of elastic projections 32 are disposed in the annular gap 24 180 degrees apart from each other in the circumferential direction. An area of an outer peripheral surface of the small-diameter cylindrical portion 13a corresponding to the elastic projections 32 are chamfered. Therefore, the elastic projections 32 are elastically deformable inward in a radial direction. An engageable claw 33 is formed in an outer surface of a distal end portion of the elastic projection 32 such that the engageable claw 33 is protruded outward in the radial direction. The engageable claws 33 are engaged with the ratchet teeth 31.

The tubes 5, 5' are connected using the connecting structure for medical use having the features mentioned above in the following manner. As shown in the upper portion of FIG. 5, the male luer portion 11 of the male assembly 1 and the female luer portion 2a of the female connector 2 are aligned and brought closer to each other. Then, the male luer portion 11 is inserted in the distal end portion of the female luer portion 2a. The insertion proceeds without resistance until the engageable protrusions 2c of the female connector 2 are abutted against the female screw 21a of the threadedly engageable cylinder 20 of the male assembly 1.

Figure 6B:
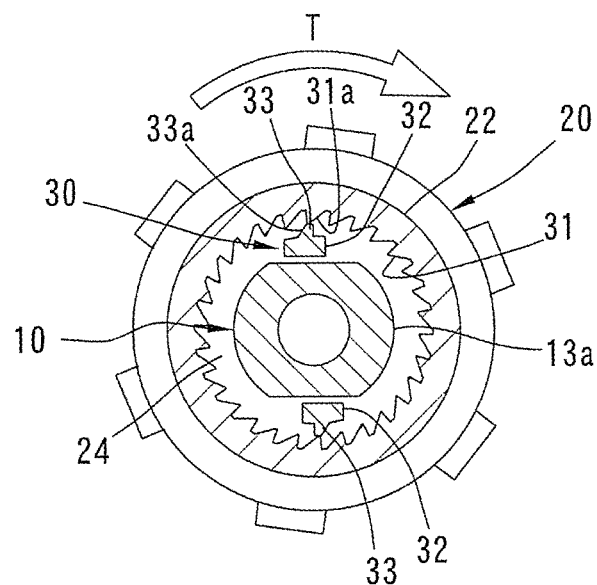
FIG. 6B is a view corresponding to FIG. 6A, showing the threadedly engageable cylinder rotated with respect to the male connector in a tightening direction.

Next, as shown in FIG. 6B, the threadedly engageable cylinder 20 is turned in a tightening direction indicated by letter T. Since inclined surfaces 33a of the engageable claws 33 slide on inclined surfaces 31a of tooth portions of the ratchet teeth 31 at this time, the engageable claws 33 are moved over the ratchet teeth 31 of the threadedly engageable cylinder 20 accompanied by elastic deformation of the elastic projections 32. Since the elastic projection 32 is long and has a small cross-sectional area, an elastic coefficient of the elastic projection 32 is small. Therefore, the threadedly engageable cylinder 20 can be turned with respect to the male connector 10 without much resistance. Thereby, the threaded engagement proceeds. As shown in the lower portion of FIG. 5, an insertion depth of the male luer portion 11 into the female luer portion 2a is increased, and the male luer portion 11 and the female luer portion 2a are joined.

When the threadedly engageable cylinder 20 is turned further in the tightening direction, the male luer portion 11 and the female luer portion 2a are closely contacted with each other. When the resistance the threadedly engageable cylinder 20 receives becomes great enough, the tightening of the threadedly engageable cylinder 20 should be stopped. In this condition, a surface 21x on a deeper side of a screw thread of the female screw 21a of the threadedly engageable cylinder 20 is abutted against the engageable protrusions 2c of the female connector 2 as shown in the lower portion of FIG. 5.

Even when an unintentional torque in a loosening direction is applied to the threadedly engageable cylinder 20, the threadedly engageable cylinder 20 is prohibited from being rotated in the loosening direction with respect to the female connector 2. It is because steep surfaces 31b of the tooth portions of the ratchet teeth 31 are caught by steep surfaces 33b of the engageable claws 33 as shown in FIG. 6A.

As mentioned above, the threadedly engageable cylinder 20 is not rotated in the loosening direction with respect to the male connector 10 after the joining of the male luer portion 11 and the female luer portion 2a is completed. Therefore, the surface 21x on the deeper side of the screw thread of the female screw 21a of the threadedly engageable cylinder 20 is maintained in the abutted state against the engageable protrusions 2c of the female connector 2 as shown in the lower portion of FIG. 5. As a result, the female luer portion 2a and the male luer portion 11 are not displaced in a separating direction even when a pressure of fluid flowing in the connecting structure is high, and sufficient sealing properties can be maintained, and thereby, leakage of the fluid can be prohibited.

To disconnect the tubes 5, 5', the female connector 2 should be turned in the loosening direction with respect to the male assembly 1. Thereby, the female connector 2 and the threadedly engageable cylinder 20 can be released from the threadedly engaged state, and the male luer portion 11 and the female luer portion 2a can be released from the joined state.

In this embodiment, the loosening prevention mechanism 30 is disposed inside of the mounting portion 22 of the threadedly engageable cylinder 20 in the radial direction instead of being exposed outside. Therefore, settling of dust on the loosening prevention mechanism 30 can be constrained to the minimum.

Other embodiments of the present invention will be described hereinafter with reference to the drawings. Same or similar reference numerals are used to designate parts that correspond to those in foregoing embodiments, and description thereof will be omitted.

Figure 7:
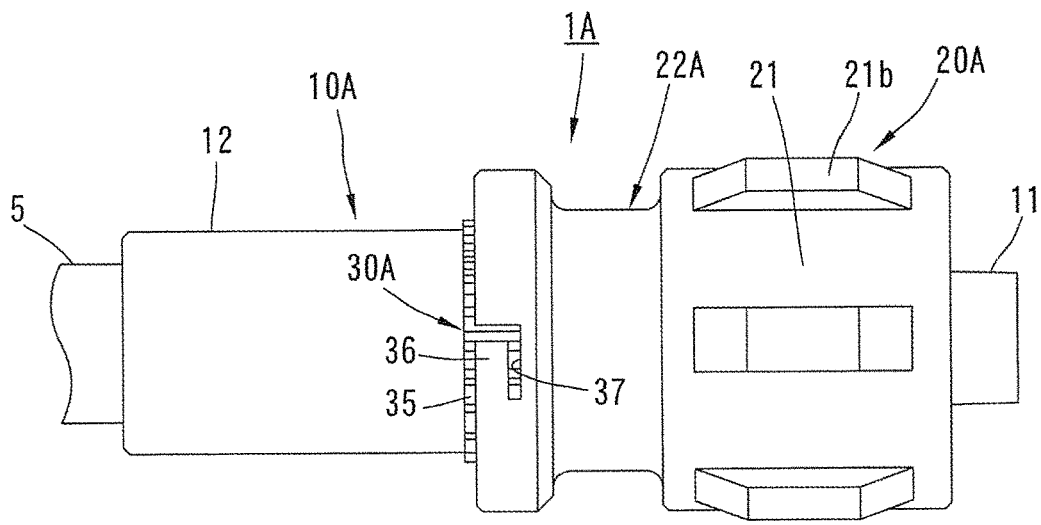
FIG. 7 is a plan view of a male assembly of a connecting structure for medical use according to a second embodiment of the present invention.
Figure 8:
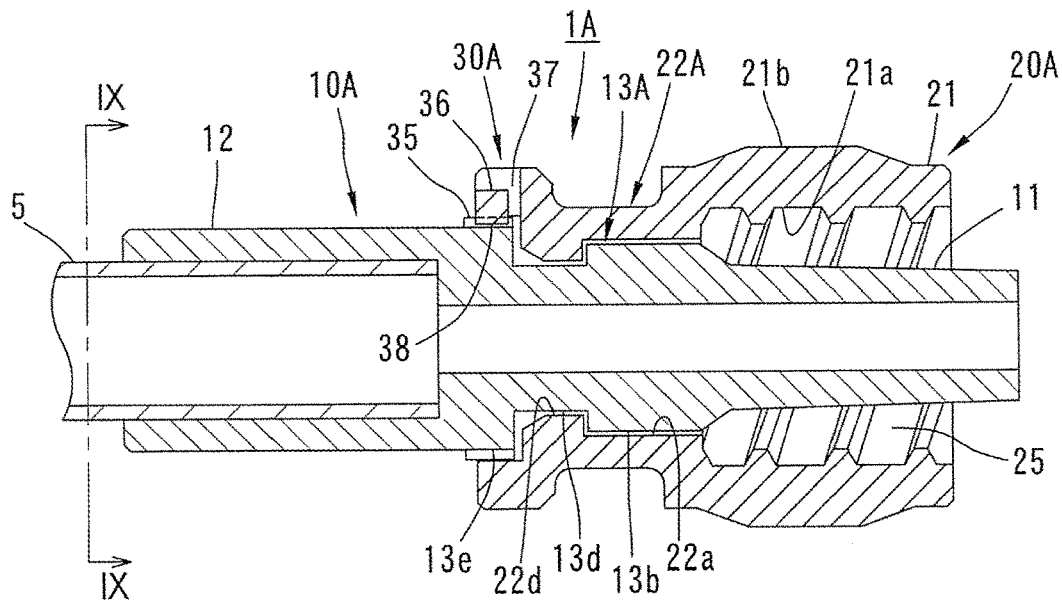
FIG. 8 is a longitudinal sectional view of the male assembly of the second embodiment.
Figure 9:
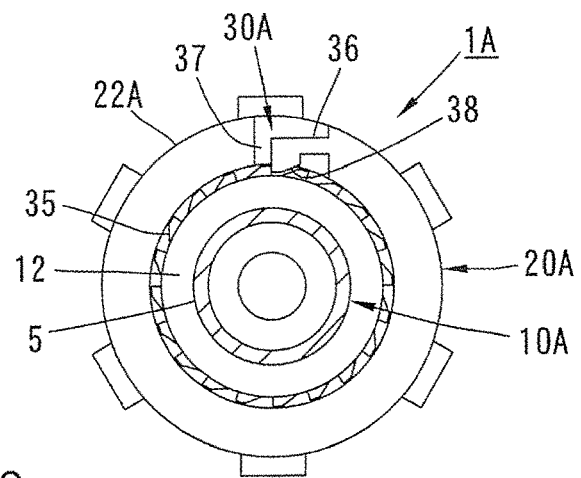
FIG. 9 is a cross-sectional view taken along line IX-IX of FIG. 8.
Figure 10:
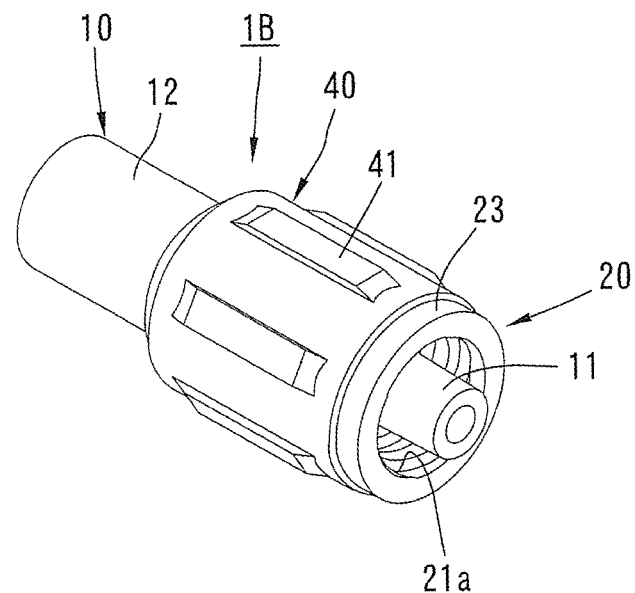
FIG. 10 is a perspective view of a male assembly of a connecting structure for medical use according to a third embodiment of the present invention.
Figure 11:
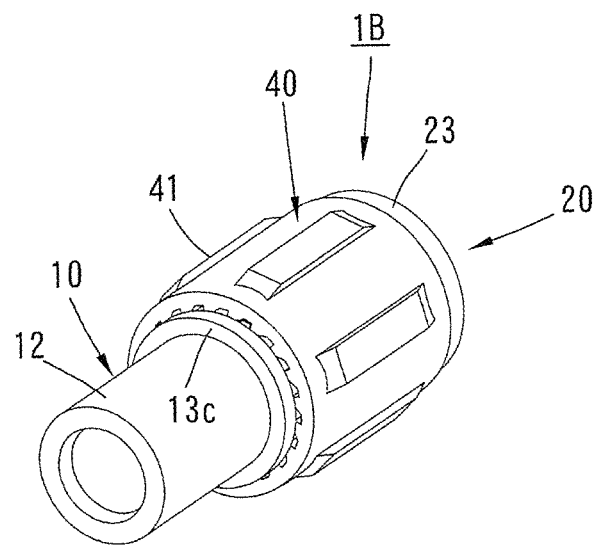
FIG. 11 is a perspective view of the male assembly of the third embodiment, viewed from a different direction from that of FIG. 10.
Figure 12:
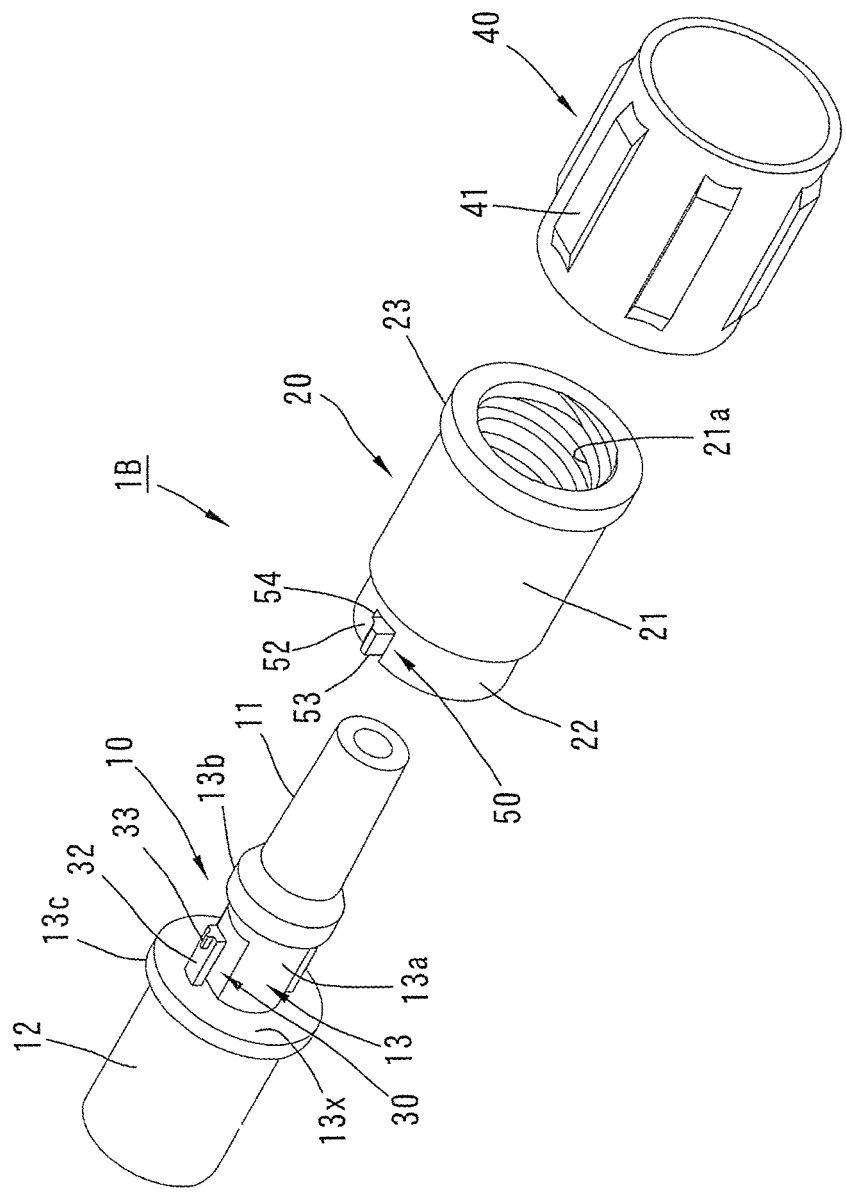
FIG. 12 is an exploded perspective view of the male assembly of the third embodiment.
Figure 13:
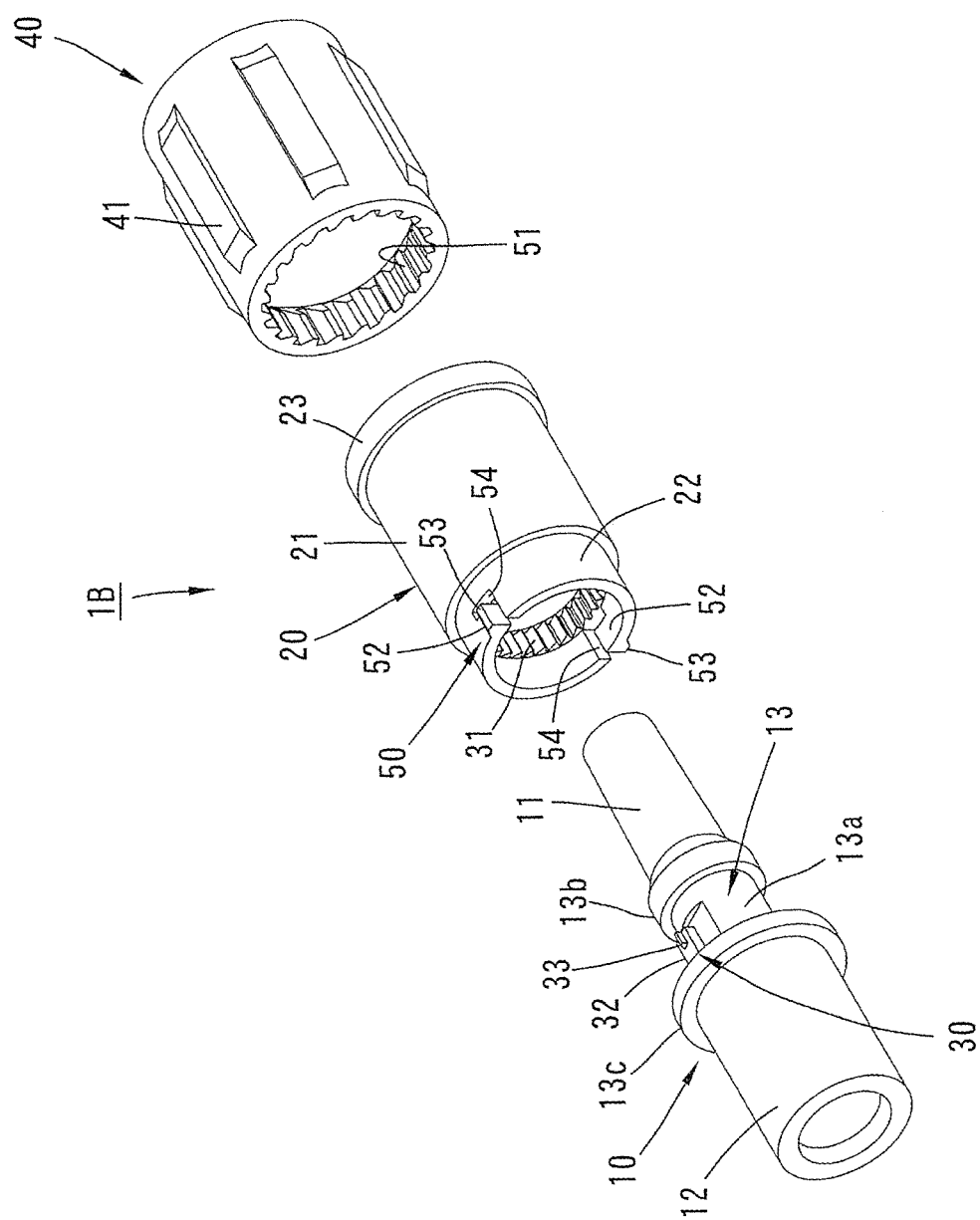
FIG. 13 is an exploded perspective view of the male assembly of the third embodiment, viewed from a different direction from that of FIG. 12.
Figure 14:
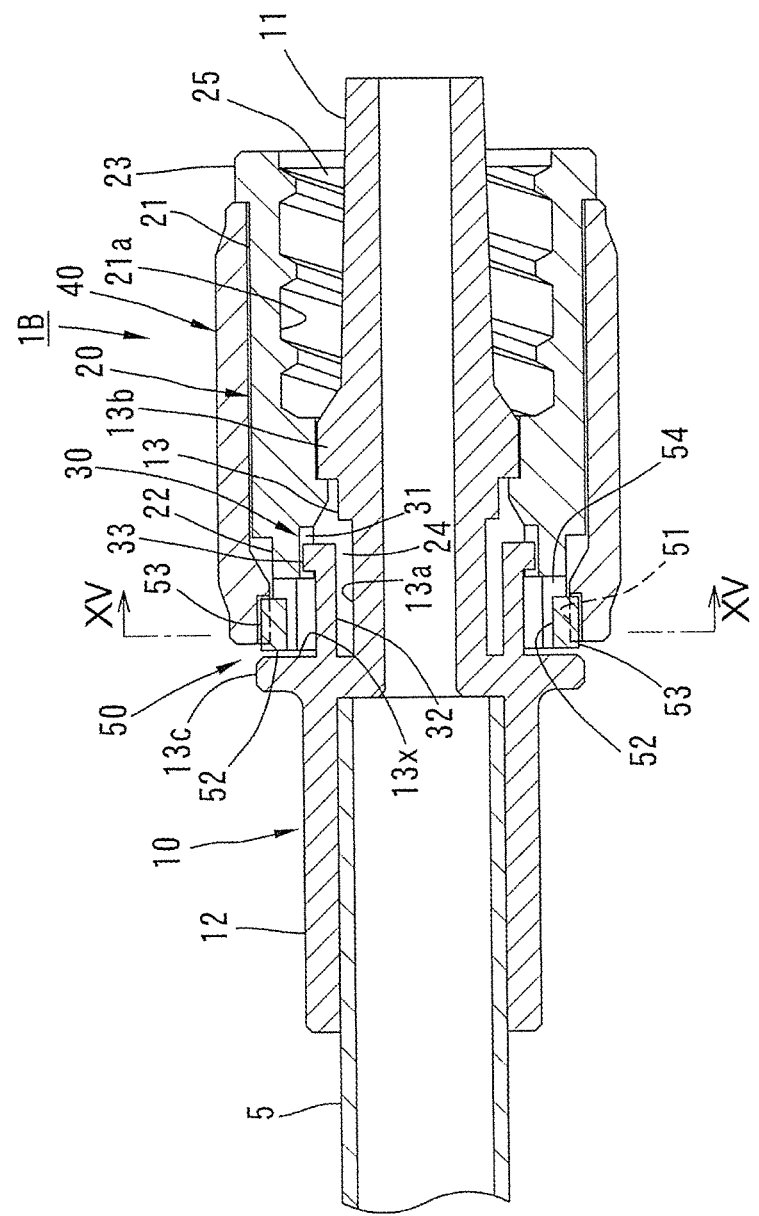
FIG. 14 is a longitudinal sectional view of the male assembly of the third embodiment.

FIGS. 7 to 9 show a male assembly 1A of a connecting structure for medical use according to a second embodiment of the present invention. Of components of the male assembly 1A, a support portion 13A of a male connector 10A, a mounting portion 22A of a threadedly engageable cylinder 20A and a loosening prevention mechanism 30A are different from those of the first embodiments.

The support portion 13A includes an annular protrusion 13b, an annular fitting groove 13d and an annular shoulder portion 13e that continues to a coupling portion 12 arranged in a direction from a male luer portion 11 to the coupling portion 12 in this order.

An annular abutment surface 22a and an annular catch protrusion 22d are formed in an inner periphery of the mounting portion 22A arranged in a direction from a female screw 21a to a basal end of the mounting portion 22A in this order. The catch protrusion 22d is fitted in the fitting groove 13d, and thereby the threadedly engageable cylinder 20A is supported by the male connector 10A such that the threadedly engageable cylinder 20A is rotatable but immovable in an axial direction. An end portion of the mounting portion 22A is disposed outside of the shoulder portion 13e of the male connector 10A in a radial direction.

The loosening prevention mechanism 30A includes ratchet teeth 35 formed in an outer periphery of the annular shoulder portion 13e of the male connector 10A over the entire periphery and an elastic projection 36 formed in the mounting portion 22A of the threadedly engageable cylinder 20A. More specifically, a slit 37 having a L-shaped configuration is formed in the end portion of the mounting portion 22A. The slit 37 includes a longitudinal portion extending in an axial direction from an end surface of the mounting portion 22A and a lateral portion extending in a circumferential direction form a deep end of the longitudinal portion. The elastic projection 36 is defined by the slit 37.

The elastic projection 36 extends in a circumferential direction. The elastic projection 36 has an engageable claw 38 formed in an inner surface of a distal end portion thereof. The engageable claw 38 is protruded inwardly in the radial direction and is engaged with the ratchet teeth 35.

As with the first embodiment, each of tooth portions of the ratchet teeth 35 includes an inclined surface and a catch surface and the engageable claw 38 includes an inclined surface and a catch surface.

In the second embodiment, arrangement of the ratchet teeth 35, the elastic projection 36 and the engageable claw 38 of the loosening prevention mechanism 30A is opposite to that of the first embodiment. However, these components work in the same way as in the first embodiment, and therefore, description thereof will be omitted.

FIGS. 10 to 15 show a connecting structure for medical use according to a third embodiment. A male connector 10, a threadedly engageable cylinder 20 and a loosening prevention mechanism 30 of a male assembly 1B of the connecting structure are substantially the same as those of the first embodiment. However, unlike in the first embodiment, a threadedly engageable portion 21 of the threadedly engageable cylinder 20 does not have elongated raised portions formed in an outer periphery thereof. Instead, the outer periphery of the threadedly engageable portion 21 is a circular cylindrical surface. An annular protrusion 23 is formed in an outer periphery of a distal end portion of the threadedly engageable portion 21.

The male assembly 1B of the third embodiment further includes an operation cylinder 40 and a torque limiting mechanism 50. The operation cylinder 40 is mounted on the outer periphery of the threadedly engageable portion 21 of the threadedly engageable cylinder 20. Opposite ends of the operation cylinder 40 are respectively caught by the annular protrusion 23 of the threadedly engageable cylinder 20 and a flange portion 13c of the male connector 10. Thereby, the operation cylinder 40 is supported so as to be immovable with respect to the threadedly engageable cylinder 20 in an axial direction.

Elongated raised portions 41 for placing fingers thereon are formed in an outer periphery of the operation cylinder 40. The elongated raised portions 41 are arranged in a circumferential direction at an even interval.

The torque limiting mechanism 50 is formed between a mounting portion 22 of the threadedly engageable cylinder 20 and a basal end portion of the operation cylinder 40. Specifically, engageable teeth 51 are formed in an inner periphery of the basal end portion of the operation cylinder 40 over the entire periphery. The engageable teeth 51 have a similar shape to ratchet teeth 31 of the loosening prevention mechanism 30.

A pair of slits 54 having a L-shaped configuration are formed in an end portion of the mounting portion 22 of the threadedly engageable cylinder 20 180 degrees apart from each other in the circumferential direction. The slit 54 includes a longitudinal portion extending in the axial direction from an end surface of the mounting portion 22 and a lateral portion extending in the circumferential direction form a deep end of the longitudinal portion. A second elastic projection 52 extending in the circumferential direction is defined by the slit 54. Since a dimension of the second elastic projection 52 in the circumferential direction is small, an elastic coefficient of the second elastic projection 52 is much larger than that of an elastic projection 32 of the loosening prevention mechanism 30.

A second engageable claw 53 is formed in an outer surface of a distal end portion of the second elastic projection 52. The second engageable claw 53 is protruded outward in a radial direction and engaged with the engageable teeth 51. The ratchet teeth 31 of the loosening prevention mechanism 30 are disposed adjacent to the second elastic projection 52 in the axial direction.

Figure 15A:
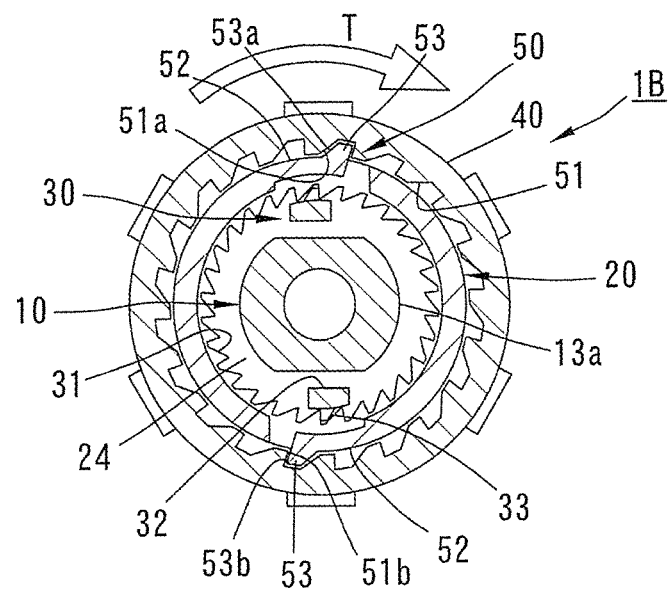
FIG. 15A is a cross-sectional view taken along line XV-XV of FIG. 14, showing the male assembly in a state in which a torque from an operation cylinder is transmitted to a threadedly engageable cylinder and a male connector via a torque limiting mechanism.

In the connecting structure having the features mentioned above, a female connector 2 is brought closer to the male assembly 1B (see FIG. 5), and a male luer portion 11 is inserted in a female luer portion 2a. In this condition, if the operation cylinder 40 is turned in a tightening direction T, a torque of the operation cylinder 40 is transmitted to the threadedly engageable cylinder 20 via the torque limiting mechanism 50. Since the elastic coefficient of the second elastic projection 52 of the torque limiting mechanism 50 is large, the engageable teeth 51 and the second engageable claws 53 are maintained in the engaged state with inclined surfaces 51a of tooth portions of the engageable teeth 51 of the torque limiting mechanism 50 and inclined surfaces 53a of the second engageable claws 53 respectively abutted against one another as shown in FIG. 15A. Therefore, the operation cylinder 40 and the threadedly engageable cylinder 20 are rotated together.

The operation cylinder 40 and the threadedly engageable cylinder 20 are rotated in the tightening direction T with respect to the male connector 10. It is because resistance of the loosening prevention mechanism 30 is small. As a result, engagement between a female screw 21a and engageable protrusions 2c proceeds, and the male luer portion 11 and the female luer portion 2a are joined with a pressing force working therebetween. In this way, the male luer portion 11 and the female luer portion 2a can be joined with sufficient sealing properties.

Figure 15B:
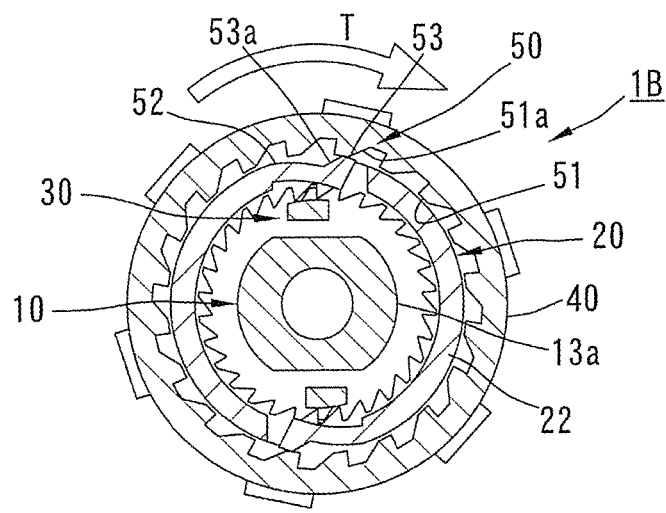
FIG. 15B is a view corresponding to FIG. 15A, showing the operation cylinder turning idly because a tightening torque of the operation cylinder exceeds a predetermined torque and the torque cannot be transmitted via the torque limiting mechanism.

When the operation cylinder 40 is turned further and the torque thereof exceeds a predetermined torque, the inclined surfaces 53a of the second engageable claws 53 are slid on the inclined surfaces 51a of the tooth portions of the engageable teeth 51 as shown in FIG. 15B. Then the second engageable claws 53 are moved over the engageable teeth 51 of the operation cylinder 40 accompanied by elastic deformation of the second elastic projections 52. In this condition, the operation cylinder 40 is turned idly with respect to the threadedly engageable cylinder 20, and therefore, rotary torque of the operation cylinder 40 is not transmitted to the threadedly engageable cylinder 20. As a result, excessive torque is not imparted to the threadedly engageable cylinder 20, and excessive pressing force can be avoided between the male luer portion 11 and the female luer portion 2a. Therefore, breakage of the male luer portion 11 and the female luer portion 2a can be prevented, and the male luer portion 11 and the female luer portion 2a can be prevented from being inseparably locked with each other.

To disconnect tubes 5, 5' after connecting the tubes 5, 5' in this manner, the operation cylinder 40 is turned in a loosening direction. Then, steep catch surfaces 51b of the tooth portions of the engageable teeth 51 of the operation cylinder 40 are respectively abutted against steep catch surfaces 53b of the second engageable claws 53 of the threadedly engageable cylinder 20, and the threadedly engageable cylinder 20 and the male connector 10 are rotated in the loosening direction together with the operation cylinder 40. As a result, the male luer portion 11 and the female luer portion 2b are released from the joined state.

Figure 16:
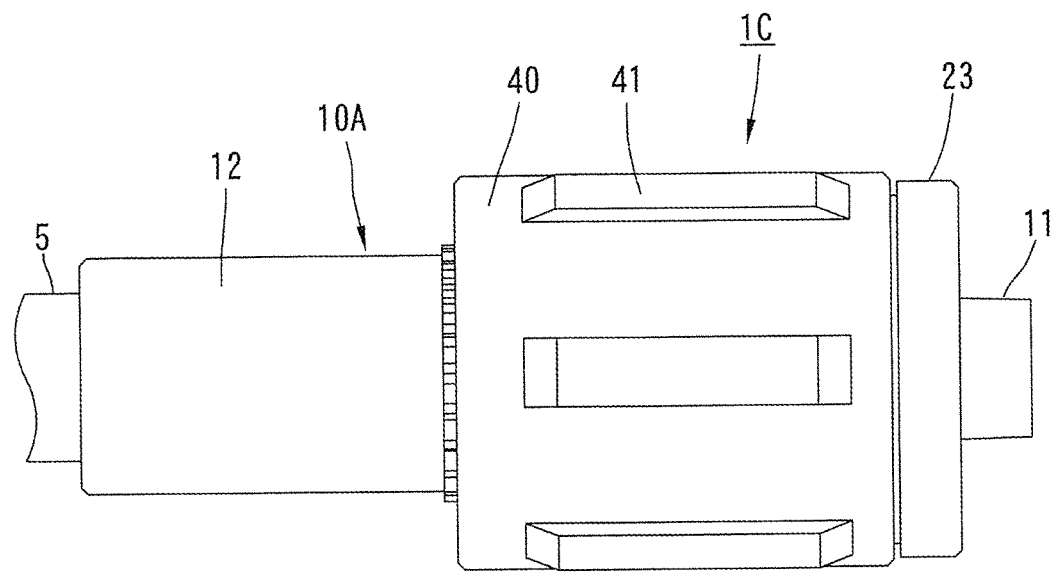
FIG. 16 is a plan view of a male assembly according to a fourth embodiment of the present invention.
Figure 17:
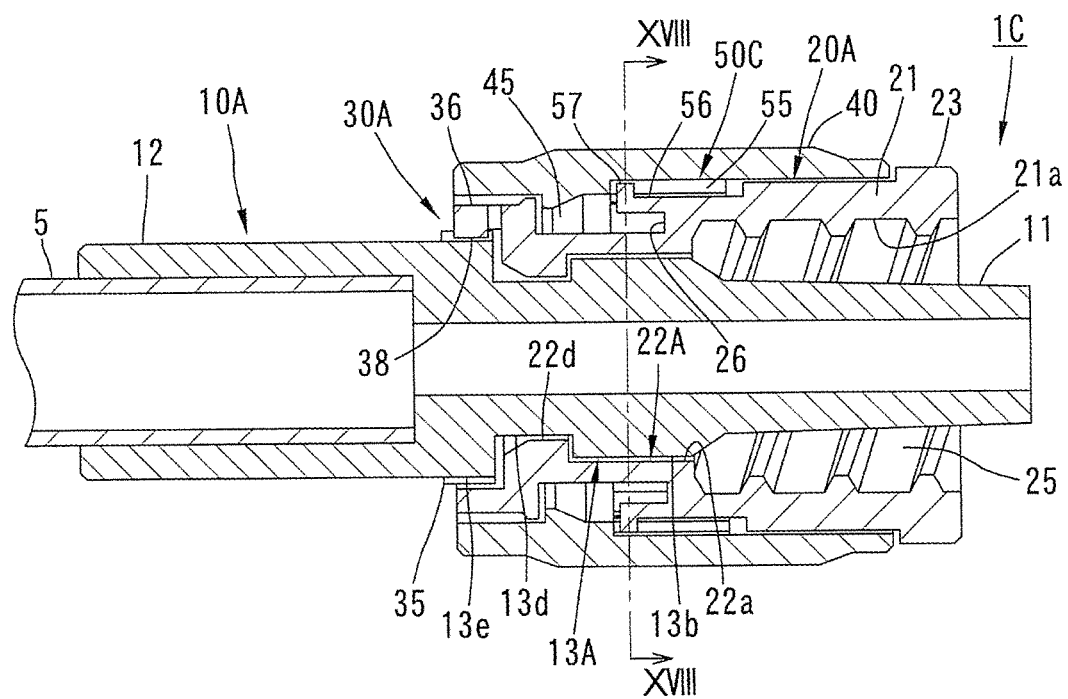
FIG. 17 is a longitudinal sectional view of the male assembly of the fourth embodiment.
Figure 18A:
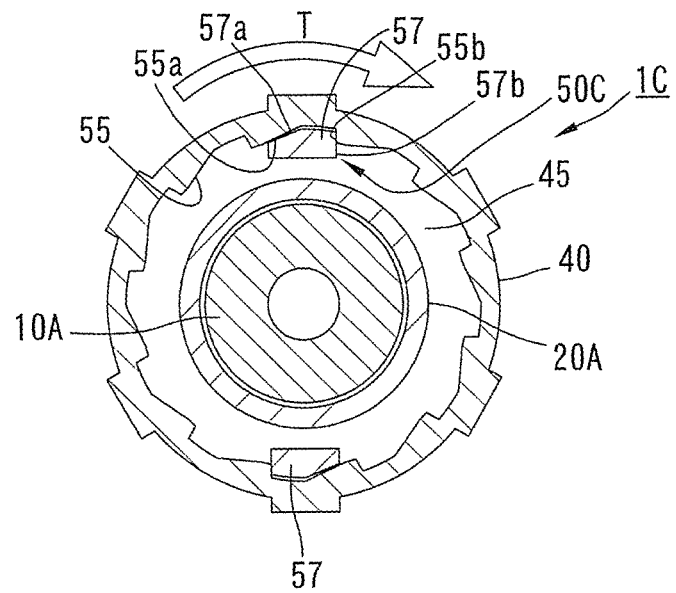
FIG. 18A is a cross-sectional view taken along line XVIII-XVIII of FIG. 17, showing the male assembly in a state in which a torque from an operation cylinder is transmitted to a threadedly engageable cylinder and a male connector via a torque limiting mechanism.

FIGS. 16 to 18 show a male assembly 1C of a connecting structure for medical use according to a fourth embodiment of the present invention. A male connector 10A, a threadedly engageable cylinder 20A and a loosening prevention mechanism 30A of the male assembly 1C are substantially same as those of the second embodiment. However, unlike that of the second embodiment, an outer periphery of a threadedly engageable portion 21 of the threadedly engageable cylinder 20A does not have elongated protrusions formed therein. The outer periphery of the threadedly engageable portion 21 is a circular cylindrical surface. An annular protrusion 23 is formed in an outer periphery of a distal end portion of the threadedly engageable portion 21.

The male assembly 1C of the fourth embodiment further includes an operation cylinder 40 and a torque limiting mechanism 50C. The operation cylinder 40 is mounted on the threadedly engageable cylinder 20A so as to be immovable in an axial direction. An annular gap 45 is formed between the operation cylinder 40 and the threadedly engageable cylinder 20A.

Engageable teeth 55 facing the annular gap 45 are formed in an intermediate portion of an inner periphery of the operation cylinder 40 over the entire periphery. On the other hand, an annular support surface 26 facing the annular gap 45 and extending in a radial direction is formed in an intermediate portion of the threadedly engageable cylinder 20A. A second elastic projection 56 extends in the axial direction from the support surface 26 in an opposite direction from a female screw 21a. A second engageable claw 57 is formed in an outer surface of a distal end portion of the second elastic projection 56. The second engageable claw 57 is protruded outward in the radial direction and engaged with the engageable teeth 55.

In the torque limiting mechanism 50C, as with the torque limiting mechanism 50 of the third embodiment, each of tooth portions of the engageable teeth 55 includes an inclined surface 55a and a catch surface 55b and the second engageable claw 57 includes an inclined surface 57a and a catch surface 57b.

The torque limiting mechanism 50C of the male assembly 1C works in a similar manner to the torque limiting mechanism 50 of the third embodiment. To describe it briefly, a torque of the operation cylinder 40 is transmitted to the threadedly engageable cylinder 20A through the torque limiting mechanism 50C, and the operation cylinder 40 and the threadedly engageable cylinder 20A are rotated in a tightening direction T with respect to the male connector 10A. It is because resistance of the loosening prevention mechanism 30A is small. As a result, engagement between the threadedly engageable cylinder 20A and the female connector 2 (see FIG. 5) proceeds, and the male luer portion 11 and the female luer portion 2a can be joined with sufficient sealing properties.

Figure 18B:
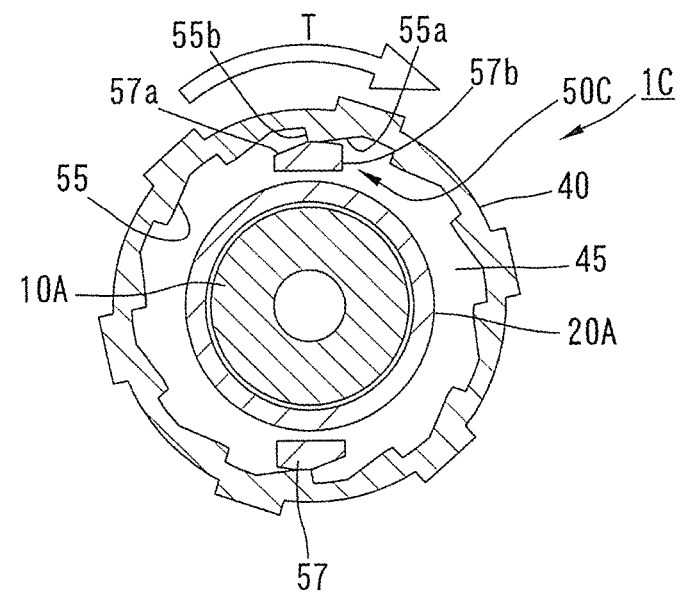
FIG. 18B is a view corresponding to FIG. 18A, showing the operation cylinder turning idly because a tightening torque of the operation cylinder exceeds a predetermined torque and the torque cannot be transmitted via the torque limiting mechanism.

When the operation cylinder 40 is turned further and the torque thereof exceeds a predetermined torque, the inclined surfaces 57a of the second engageable claws 57 are respectively slid on the inclined surfaces 55a of the tooth portions of the engageable teeth 55 as shown in FIG. 18B. Then the second engageable claws 57 are moved over the engageable teeth 55 of the operation cylinder 40 accompanied by elastic deformation of the second elastic projections 56. As a result, the operation cylinder 40 is turned idly with respect to the threadedly engageable cylinder 20A, and therefore, tightening by excessive torque can be avoided.

To disconnect tubes, the operation cylinder 40 is turned in a loosening direction. Then, steep catch surfaces 55b of the engageable teeth 55 of the operation cylinder 40 are abutted against steep catch surfaces 57b of the second engageable claws 57 of the threadedly engageable cylinder 20A, and the threadedly engageable cylinder 20A and the male connector 10A are rotated in the loosening direction together with the operation cylinder 40.

Figure 19:
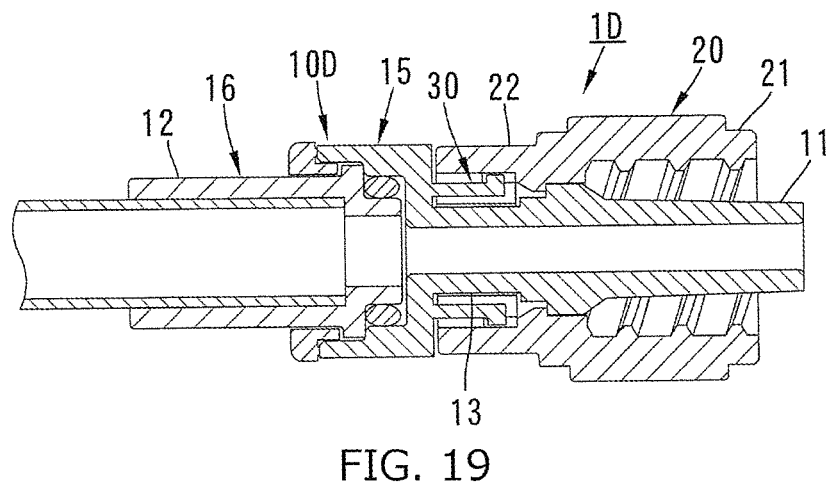
FIG. 19 is a cross-sectional view of a male assembly of a connecting structure for medical use according to a fifth embodiment of the present invention.

In a male assembly 1D of a fifth embodiment shown in FIG. 19, a male connector 10D includes a connector body 15 and a coupling member 16 rotatably coupled to the connector body 15. The connector body 15 includes a male luer portion 11 and a mounting portion 13. The coupling member 16 includes a coupling portion 12. Other features of the fifth embodiment are similar to those of the first embodiment. The male connector 10D may also be adopted in the second to the fourth embodiments.

Figure 20:
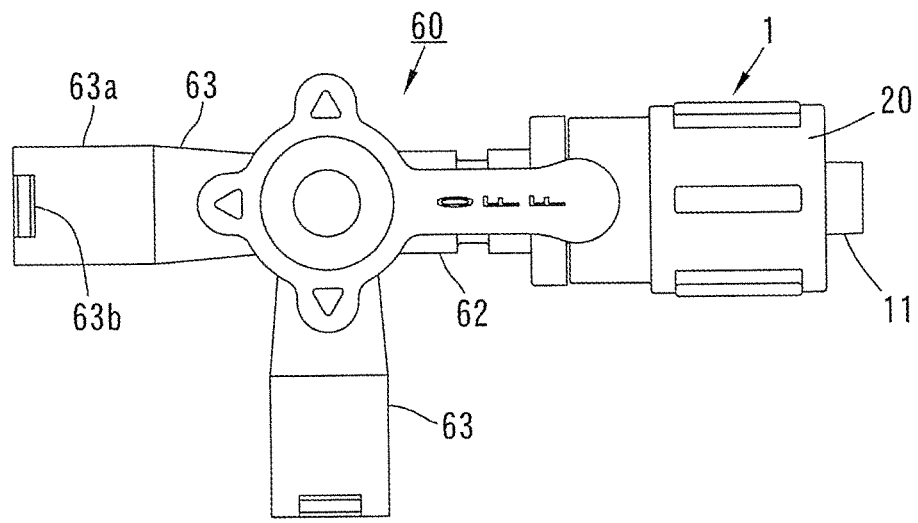
FIG. 20 is a plan view of a three-way stopcock incorporating a male assembly of a connecting structure for medical use according to a sixth embodiment of the present invention.
Figure 21:
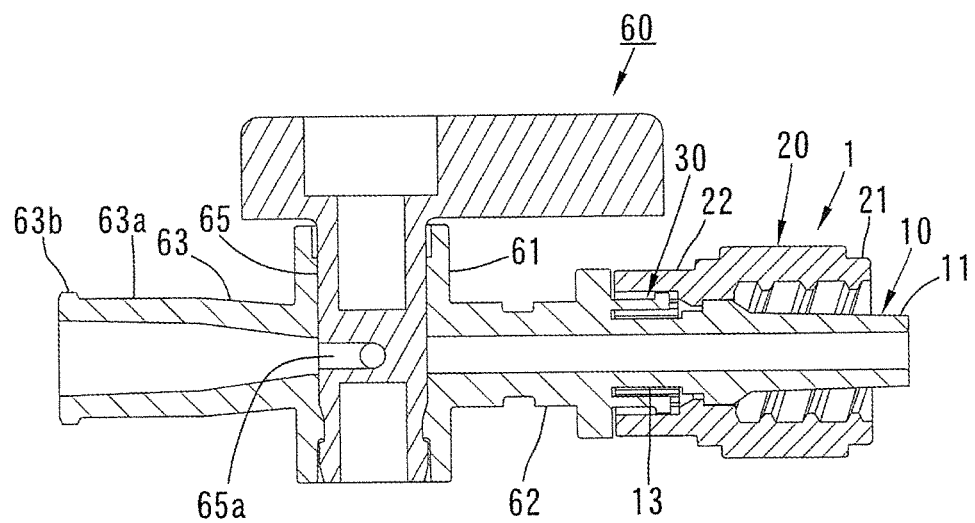
FIG. 21 is a cross-sectional view of the three-way stopcock.
Figure 22:
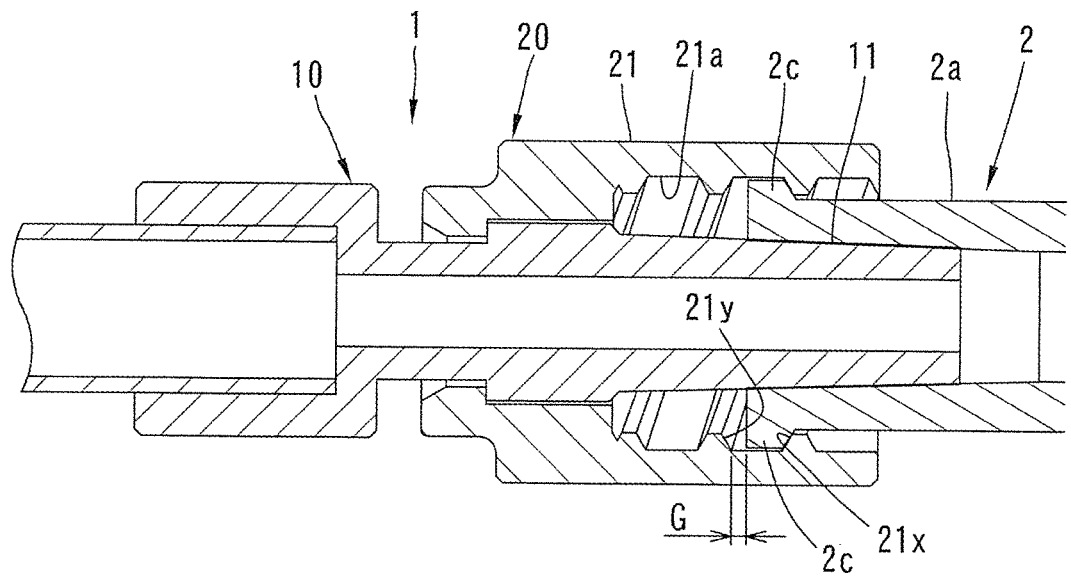
FIG. 22 is a cross-sectional view of a conventional connecting structure for medical use, showing the connecting structure in a state in which connection of a male luer portion and a female luer portion by tightening a threadedly engageable cylinder is completed.
Figure 23:
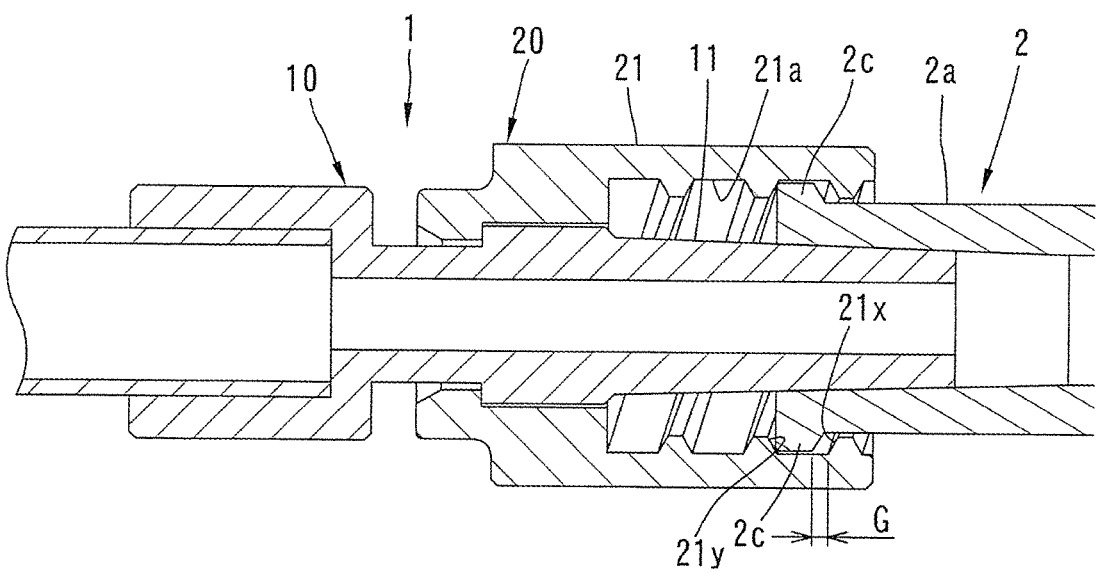
FIG. 23 is a view corresponding to FIG. 22, showing the threadedly engageable cylinder rotated in a loosening direction.

In a sixth embodiment shown in FIGS. 20 and 21, the present invention is applied in a three-way stopcock 60 (stopper cock). The three-way stopcock 60 includes a body 61 having a cylindrical configuration and three flow tubular portions 62, 63, 63 integrally formed with the body 61. One flow tubular portion 62 has a male assembly 1 similar to that of the first embodiment mounted in a distal end portion thereof. A male connector 10 of the male assembly 1 is integral with the flow tubular portion 62. Female luer portions 63a and engageable protrusions 63b are formed in distal end portions of the other two flow tubular portions 63, 63.

A cock member 65 is received in the body 61. The cock member 65 includes a communication passage 65a having a L-shaped configuration. The cock member 65 selectively makes two of passages of the flow tubular portions 62, 63, 63 communicate with each other by turning operation.

The male assembly of the second to the fourth embodiments may be mounted on the three-way stop cock.

The present invention is not limited to the embodiments described above. Various modifications can be made without departing from the scope and spirit of this invention. Features of many of the embodiments mentioned above may be combined with other features of other embodiments.

The present invention may also be applied to connecting structures for connecting medical components other than a tube and a stopcock.

INDUSTRIAL APPLICABILITY

The present invention may be applied to connecting structures for medical components.

The invention claimed is:
1. A connecting structure for medical use comprising:
a male assembly; and
a female connector having a cylindrical configuration,
the male assembly including a male connector having a cylindrical configuration and a threadedly engageable cylinder rotatably coupled to the male connector, the male connector including a male luer portion and a support portion arranged in a direction from a distal end to a basal end of the male connector in this order, the threadedly engageable cylinder including a threadedly engageable portion and a mounting portion arranged in a direction from a distal end to a basal end of the threadedly engageable cylinder in this order, the mounting portion rotatably mounted to an outer periphery of the support portion of the male connector, the threadedly engageable portion having a female screw in an inner periphery thereof, the threadedly engageable portion disposed outside of the male luer portion in a radial direction, the female connector including a female luer portion and an engageable protrusion formed in an outer periphery of the female luer portion, the male luer portion and the female luer portion joined by turning the threadedly engageable cylinder in a tightening direction in a state where the female screw of the threadedly engageable cylinder is threadedly engaged with the engageable protrusion of the female connector, wherein a loosening prevention mechanism is disposed between the support portion of the male connector and the mounting portion of the threadedly engageable cylinder, the loosening prevention mechanism prohibiting the threadedly engageable cylinder from being rotated in a loosening direction with respect to the male connector in a state where the male luer portion and the female luer portion are joined, wherein the loosening prevention mechanism includes:
ratchet teeth formed in one of the support portion of the male connector and the mounting portion of the threadedly engageable cylinder over an entire periphery;
at least one elastic projection formed in the other of the support portion and the mounting portion; and
an engageable claw formed in a free end of the elastic projection and engageable with the ratchet teeth.

2. The connecting structure for medical use according to claim 1, wherein:
an annular gap is formed between the support portion of the male connector and the mounting portion of the threadedly engageable cylinder;
the ratchet teeth facing the annular gap are formed in an inner periphery of the mounting portion of the threadedly engageable cylinder;
the elastic projection is formed in the support portion of the male connector and disposed in the annular gap; and
the engageable claw is protruded outwardly in a radial direction from the free end of the elastic projection and engaged with the ratchet teeth.

3. The connecting structure for medical use according to claim 2, wherein:
the support portion of the male connector includes a support surface facing the annular gap and extending in the radial direction; and
the elastic projection extends in an axial direction of the male connector from the support surface.

4. The connecting structure for medical use according to claim 1, wherein:
the ratchet teeth are formed in an outer periphery of the support portion of the male connector;
the elastic projection is formed in the mounting portion of the threadedly engageable cylinder; and
the engageable claw is protruded inwardly in a radial direction and engaged with the ratchet teeth.

5. The connecting structure for medical use according to claim 4, wherein:
a slit having a L-shaped configuration is formed in an end portion of the mounting portion of the threadedly engageable cylinder; and
the elastic projection extending in a circumferential direction is defined by the slit.

6. A connecting structure for medical use comprising:
a male assembly; and
a female connector having a cylindrical configuration,
the male assembly including a male connector having a cylindrical configuration and a threadedly engageable cylinder rotatably coupled to the male connector,
the male connector including a male luer portion and a support portion arranged in a direction from a distal end to a basal end of the male connector in this order,
the threadedly engageable cylinder including a threadedly engageable portion and a mounting portion arranged in a direction from a distal end to a basal end of the threadedly engageable cylinder in this order, the mounting portion rotatably mounted to an outer periphery of the support portion of the male connector, the threadedly engageable portion having a female screw in an inner periphery thereof, the threadedly engageable portion disposed outside of the male luer portion in a radial direction,
the female connector including a female luer portion and an engageable protrusion formed in an outer periphery of the female luer portion,
the male luer portion and the female luer portion joined by turning the threadedly engageable cylinder in a tightening direction in a state where the female screw of the threadedly engageable cylinder is threadedly engaged with the engageable protrusion of the female connector,
wherein a loosening prevention mechanism is disposed between the support portion of the male connector and the mounting portion of the threadedly engageable cylinder, the loosening prevention mechanism prohibiting the threadedly engageable cylinder from being rotated in a loosening direction with respect to the male connector in a state where the male luer portion and the female luer portion are joined,
further comprising:
an operation cylinder mounted on an outer periphery of the threadedly engageable cylinder; and
a torque limiting mechanism disposed between the threadedly engageable cylinder and the operation cylinder, wherein:
the torque limiting mechanism transmits a rotary torque in a tightening direction of the operation cylinder to the threadedly engageable cylinder; and
the torque limiting mechanism allows the operation cylinder to turn idly with respect to the threadedly engageable cylinder when the rotary torque exceeds a predetermined torque.

7. The connecting structure for medical use according to claim 1, further comprising:
an operation cylinder mounted on an outer periphery of the threadedly engageable cylinder; and
a torque limiting mechanism disposed between the threadedly engageable cylinder and the operation cylinder, wherein:
the torque limiting mechanism transmits a rotary torque in a tightening direction of the operation cylinder to the threadedly engageable cylinder;

the torque limiting mechanism allows the operation cylinder to turn idly with respect to the threadedly engageable cylinder when the rotary torque exceeds a predetermined torque;

the torque limiting mechanism includes engageable teeth formed in one of the threadedly engageable cylinder and the operation cylinder over an entire periphery, at least one second elastic projection formed in the other of the threadedly engageable cylinder and the operation cylinder and second engageable claw formed in the second elastic projection and engaged with the engageable teeth; and an elastic coefficient of the second elastic projection is greater than an elastic coefficient of the elastic projection of the loosening prevention mechanism.

8. The connecting structure for medical use according to claim 7, wherein:

the engageable teeth are formed in an inner periphery of the operation cylinder;

the second elastic projection is formed in the threadedly engageable cylinder; and the second engageable claw is protruded outwardly in a radial direction and engaged with the engageable teeth.

9. The connecting structure for medical use according to claim 8, wherein:

a slit having a L-shaped configuration is formed in an end portion of the mounting portion of the threadedly engageable cylinder;

the second elastic projection of the torque limiting mechanism is defined by the slit;

the ratchet teeth of the loosening prevention mechanism are formed in an inner periphery of the mounting portion of the threadedly engageable cylinder and disposed adjacent to the second elastic projection in an axial direction;

the elastic projection of the loosening prevention mechanism is formed in the support portion of the male connector; and the engageable claw is protruded outwardly in a radial direction from the free end of the elastic projection and engaged with the ratchet teeth.

10. The connecting structure for medical use according to claim 8, wherein:

an annular gap is formed between the threadedly engageable cylinder and the operation cylinder;

the ratchet teeth facing the annular gap are formed in the inner periphery of the operation cylinder;

the threadedly engageable cylinder includes a support surface facing the annular gap and extending in the radial direction; and the second elastic projection extending in an axial direction of the threadedly engageable cylinder from the support surface is disposed in the annular gap.

* * * * *